(12) United States Patent
de los Reyes

(10) Patent No.: US 10,507,409 B2
(45) Date of Patent: Dec. 17, 2019

(54) HYPER-PRODUCTIVE CHROMATOGRAPHY SYSTEM AND PROCESS

(71) Applicant: SPF Technologies LLC, Somerville, MA (US)

(72) Inventor: Gaston de los Reyes, Somerville, MA (US)

(73) Assignee: SPF TECHNOLOGIES, LLC, Somerville, MA (US)

(*) Notice: Subject to any disclaimer, the term of this patent is extended or adjusted under 35 U.S.C. 154(b) by 460 days.

(21) Appl. No.: 15/456,485

(22) Filed: Mar. 11, 2017

(65) Prior Publication Data

US 2017/0259189 A1  Sep. 14, 2017

Related U.S. Application Data

(60) Provisional application No. 62/307,467, filed on Mar. 12, 2016.

(51) Int. Cl.
*B01D 15/10* (2006.01)
*B01D 15/16* (2006.01)
(Continued)

(52) U.S. Cl.
CPC .......... *B01D 15/206* (2013.01); *B01D 15/10* (2013.01); *B01D 15/163* (2013.01); *B01D 15/22* (2013.01); *B01J 20/282* (2013.01); *B01J 20/285* (2013.01); *B01J 20/28016* (2013.01); *B33Y 80/00* (2014.12); *G01N 30/48* (2013.01);
(Continued)

(58) Field of Classification Search
CPC .... B01D 15/10; B01D 15/163; B01D 15/206; B01D 15/22; B01D 15/34; B01D 15/362; B01D 15/363; B01D 15/3809; B01J 20/28016; B01J 20/282; B01J 20/283; B01J 20/285; B33Y 80/00; G01N 30/48; G01N 30/482; G01N 30/52; G01N 30/6047; G01N 30/6091; G01N 2030/486
See application file for complete search history.

(56) References Cited

U.S. PATENT DOCUMENTS 3,340,085 A  9/1967  Istvan
3,422,604 A  1/1969  Haase
(Continued)

FOREIGN PATENT DOCUMENTS

FR  2645965  10/1990
GB  WO 92/03206  3/1992
(Continued)

OTHER PUBLICATIONS

International Search Report and the Written Opinion, PCT/US2014050743, dated Nov. 20, 2014, pp. 10.
(Continued)

*Primary Examiner* — Benjamin L Lebron
(74) *Attorney, Agent, or Firm* — Barry Gaiman

(57) ABSTRACT

A hyper-productive chromatography technique includes providing a scalable and stackable chromatographic cassette, loading a sample to be processed, operating the scalable chromatographic cassette having an adsorptive chromatographic bed having a volume greater than 0.5 liter by establishing a flow at a linear velocity greater than 500 cm/hr with a residence time of the loading step of less than one minute.

21 Claims, 7 Drawing Sheets

(51) Int. Cl.

| | |
|---|---|
| *B01D 15/20* | (2006.01) |
| *B01D 15/22* | (2006.01) |
| *B01D 15/36* | (2006.01) |
| *B01D 15/38* | (2006.01) |
| *B01J 20/28* | (2006.01) |
| *B01J 20/282* | (2006.01) |
| *B01J 20/285* | (2006.01) |
| *B33Y 80/00* | (2015.01) |
| *B01J 20/281* | (2006.01) |
| *G01N 30/52* | (2006.01) |
| *G01N 30/60* | (2006.01) |
| *G01N 30/00* | (2006.01) |
| *B01J 20/283* | (2006.01) |
| *B01D 15/34* | (2006.01) |

(52) U.S. Cl.
CPC ........... *G01N 30/482* (2013.01); *G01N 30/52* (2013.01); *G01N 30/6047* (2013.01); *G01N 30/6091* (2013.01); *B01D 15/34* (2013.01); *B01D 15/362* (2013.01); *B01D 15/363* (2013.01); *B01D 15/3809* (2013.01); *B01J 20/283* (2013.01); *G01N 2030/486* (2013.01)

(56) References Cited

U.S. PATENT DOCUMENTS

| | | | |
|---|---|---|---|
| 4,971,736 A | 11/1990 | Hagen et al. | |
| 5,683,916 A * | 11/1997 | Goffe | B01D 61/00 210/198.3 |
| 5,800,706 A | 9/1998 | Fischer | |
| 7,947,175 B2 | 5/2011 | Shinkazh | |
| 7,988,859 B2 | 8/2011 | Shinkazh | |
| 9,802,979 B2 | 10/2017 | Bracewell et al. | |
| 2001/0032814 A1 | 10/2001 | Kearney et al. | |
| 2003/0150806 A1 | 8/2003 | Hobbs et al. | |
| 2003/0155300 A1* | 8/2003 | Afeyan | B01D 15/345 210/656 |
| 2005/0006293 A1 | 1/2005 | Koehler | |
| 2008/0135484 A1 | 6/2008 | Hammer | |
| 2008/0148936 A1 | 6/2008 | Baksh | |
| 2008/0236389 A1 | 10/2008 | Leedy et al. | |
| 2008/0283458 A1 | 11/2008 | Ishii | |
| 2009/0321338 A1 | 12/2009 | Natarajan | |
| 2010/0187167 A1 | 7/2010 | Reinbigler | |
| 2010/0222570 A1 | 9/2010 | Ratnam et al. | |
| 2011/0206572 A1 | 8/2011 | McKenna et al. | |
| 2011/0217539 A1 | 9/2011 | Bonner et al. | |
| 2012/0097591 A1 | 4/2012 | Berthold | |
| 2012/0118807 A1 | 5/2012 | Natarajan | |
| 2012/0309053 A1 | 12/2012 | Wellings | |
| 2013/0020263 A1 | 1/2013 | Gebauer | |
| 2013/0068671 A1 | 3/2013 | Gebauer | |
| 2013/0197200 A1* | 8/2013 | Bian | B01J 20/20 530/388.1 |
| 2014/0339170 A1* | 11/2014 | de los Reyes | B01D 15/206 210/656 |

FOREIGN PATENT DOCUMENTS

| | | |
|---|---|---|
| JP | A 2006-90813 | 4/2006 |
| JP | A2014-032134 | 2/2014 |
| WO | WO 90/05018 | 5/1990 |
| WO | WO 2012/104278 | 8/2012 |

OTHER PUBLICATIONS

Maksimova, E.F., et al. "Methacrylate-based monolithic layers for planar chromatography of polymers," Journal of Chromatography A, 1218: 2425-2431 (2011). Available online Dec. 21, 2010.

Svec, F., et al. "Molded rigid monolithic porous polymers: an inexpensive, efficient, and versatile alternative to beads for the design of materials for numerous applications," Ind. Eng. Chem. Res., 38: 34-48 (1999).

Siwak, M., et al. "Integration of a novel modular chromatography scaffold and resin design to achieve a Hyper Productive Protein A capture process". PowerPoint slides. Presented at ACS BIOT San Diego, Mar. 13-17, 2016.

Ng, Candy K.S.., et al. "Design of high productivity antibody capture by protein A chromatography using an integrated experimental and modeling approach," Journal of Chromatography B, 899 116-126 (2012). Available online May 14, 2012.

EP Supplementary Search Report, 14836168.6-1554 /3033157 , dated Mar. 24, 2017, pp. 14.

JP Office Action dated Oct. 16, 2018, Japanese Patent Application No. 2017-006413, 10 Pages.

* cited by examiner

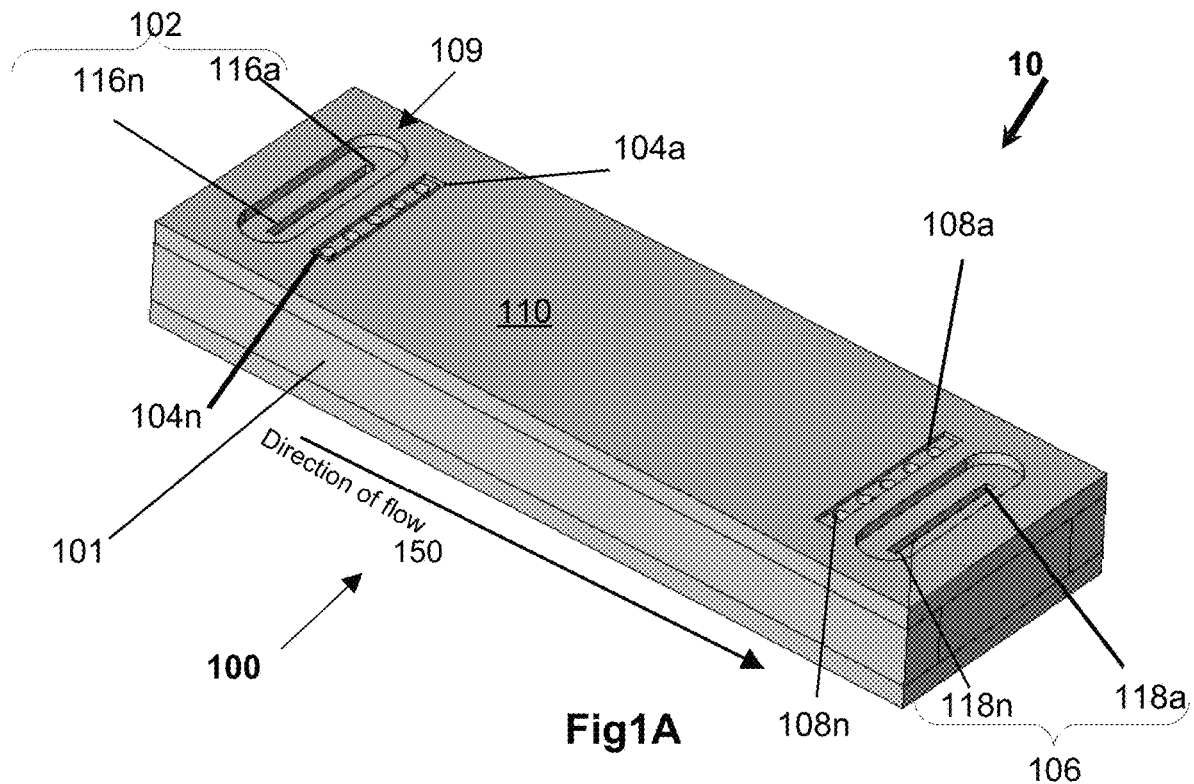
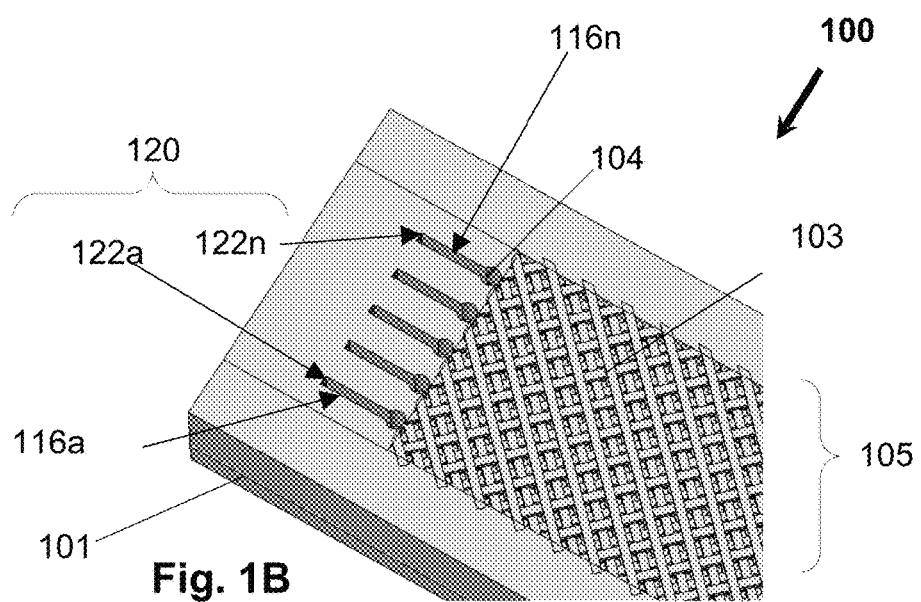

HYPER-PRODUCTIVE CHROMATOGRAPHY SYSTEM AND PROCESS

RELATED APPLICATIONS

This application claims the benefit of U.S. Provisional Application No. 62/307,467, entitled STACKABLE PLANAR ADSORPTIVE DEVICES, filed Mar. 12, 2016; which application is hereby incorporated herein by reference in its entirety.

TECHNICAL FIELD

The field of this invention is related to adsorptive devices and processes, of which chromatography is an example. More specifically, this invention relates to hyper-productive chromatography systems and processes.

BACKGROUND OF THE INVENTION

Adsorptive processes and devices are widely used in the analysis and purification of chemicals, including synthetic and naturally-derived pharmaceuticals, blood products and recombinant proteins. Chromatography is a general separation technique that relies on the relative affinity or distribution of the molecules of interest between a stationary phase and a mobile phase for molecular separation. The stationary phase typically comprises a porous media imbibed with solvent. The mobile phase comprises a solvent, which can be aqueous or organic, that flows through the interstitial space that exists between the spaces occupied by the stationary phase.

Columns with associated end caps, fittings and tubing are the most common configuration, with the media packed into the tube or column. The mobile phase is pumped through the column. The sample is introduced at one end of the column, the feed end, and the various components interact with the stationary phase by any one of a multitude of adsorptive phenomena. The differential adsorptive interaction between the components and media leads them to traverse the column at different velocities, which results in a physical separation of the components in the mobile phase. The separated components are collected or detected at the other end of the column, the eluent end, in the order in which they travel in the mobile phase. In one type of adsorptive process, referred to as capture and release process, the process involves multiple steps, first to load the media, then to wash it, and then to elute it.

Chromatographic methods include among other methods, gel chromatography, ion exchange chromatography, hydrophobic interaction chromatography, reverse phase chromatography, affinity chromatography, immuno-adsorption chromatography, lectin affinity chromatography, ion affinity chromatography and other such well-known chromatographic methods.

Adsorptive media comes in many forms, most typically in the form of chromatographic beads. The beads are conventionally packed into columns, with the column walls and ends immobilizing the beads into a fixed adsorptive bed, a bed being a porous three dimensional structure containing the stationary phase (in this case the beads) and the pore space through which the mobile phase flows/permeates (the space between the beads).

Conventional chromatographic devices require that beads must be packed into a column. The quality of this packing determines the performance of the adsorbing bed. This adds another source of variability to the chromatographic process and must be validated before use. Furthermore, beds packed with beads are prone to voiding, a phenomenon whereby the beads settle into a denser structure resulting in the creation of voids and in non-homogeneities in the packing density of the bed, all of which results in a deterioration of performance. This is especially true in columns packed with soft beads.

While it is theoretically possible to achieve high operational velocities exceeding 2000 cm/hr with rigid particles, beads such as AbSolute (Novasep Process Pompey, France) or silica beads packed in columns, it is generally not possible to use softer beads such as agarose and polymethylmethacrylate microspheres (PMMA) at high velocities exceeding 400 cm/hr.

Furthermore silica particles are not generally used to purify monoclonal antibodies. Velocities higher than 400 cm/hr are even less possible with production-scale columns having diameters of 20-200 cm (Sigma=0.02-0.2/cm). Where Sigma is a specific surface area of the adsorptive bed, defined as the surface area of solid support divided by the volume of the bed, a measure of the level of support imparted to the packed bed by the walls of the adsorptive device. In the case of a conventional column sigma equals four divided by d (where d equals the diameter of the column).

Some silica bead based processes can theoretically be run at a velocity of 2000 cm/hr, however this is not possible with agarose or PMMA beads. It is also difficult to scale up lab processes to manufacturing volumes (e.g. exceeding one liter). However, even beds packed with rigid beads may be compressible, leading to undesirable increases in pressure drop and possibly voiding if run at very high velocities.

SUMMARY

The special demands imposed on pharmaceutical manufacturing processes make it highly desirable that such processes be easily scaled-up and operated at high productivity rates. In particular, there are many advantages to processes that can be scaled-up without having to reset or redevelop the processing conditions. Such processes and devices are referred to in the industry as linearly-scalable processes and devices; in essence, the parameters that define the device and the separation process and operating conditions remain unchanged as the process moves from the laboratory bench (i.e., discovery), where the column/device can be as small as several milliliters, to the process development laboratory (e.g., columns of several liters), to clinical manufacturing, to large-scale manufacturing, where the chromatography column can be as large as several hundred liters. Existing chromatographic devices are not linearly scalable, their design and geometry requiring significant alterations as the device size increases, thereby introducing uncertainties and unwanted risks as processes evolve from drug discovery, to clinical trials, to small-scale and then to large-scale manufacturing.

One general aspect includes a method of performing a hyper-productive chromatography process including: providing a stackable chromatographic cassette, loading a sample to be processed, operating the stackable chromatographic cassette having an adsorptive chromatographic bed having a volume greater than 0.5 liter by establishing a flow at a linear velocity greater than 500 cm/hr and having a residence time of the loading step of less than one minute.

Such a technique and corresponding system allows operation of adsorptive bed to operate at higher flow rates and pressures than can be achieved with conventional devices.

Such technique also enables higher productivity with lower residence times and the use of smaller beads and softer beads than are used in conventional columns.

In other embodiments the linear velocity is greater than 1000 cm/hr; the residence time in a load step is less than 0.5 minute. In another embodiment the residence time in a load step is less than 0.25 minute. In another embodiment the residence time in a loading step is less than 0.5 minutes. In another embodiment, the chromatographic cassette is operated with a linear pressure drop over a velocity range of zero cm/hr to about 1200 cm/hr.

Other techniques include operating at a total cycle productivity of greater than about 60 g/l/hr (GLH), with media having an average bead size less than about 50 m at velocities greater than about 500 cm/hr. Still other techniques include operating at a total cycle productivity of greater than 100 g/l/hr (GLH) with media having an average bead size less than about 40 m at velocities greater than about 800 cm/hr. Another technique includes operating at a total cycle productivity of greater than 150 g/l/hr (GLH) with media having an average bead size less than about 30 m at velocities greater than about 1000 cm/hr.

The system may also include hyper-productive chromatography system and process a method of performing a hyper-productive chromatography process including: providing at least one chromatographic cassette having an adsorptive chromatographic bed having a bed volume greater than one liter and including one of: compressible chromatographic adsorptive media, semi-compressible chromatographic adsorptive media, soft chromatographic adsorptive media. The method also includes placing the at least one chromatographic cassette in a cassette holder. The method also includes loading a sample to be processed. The method also includes operating the chromatographic adsorptive bed by establishing a flow at a velocity greater than 1000 cm/hr and having a residence time in a loading step is less than one minute.

Implementations of the described techniques may include hardware, a method or process, or computer software on a computer-accessible medium. Chromatography cassettes described herein include Chromassettes® manufactured by SPF Technologies, LLC of Somerville, Mass.

BRIEF DESCRIPTION OF DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims.

FIG. 1A is a view of a stackable chromatography cassette according to embodiments disclosed herein;

FIG. 1B is a view of a lattice and distribution network for a stackable chromatography cassette according to embodiments disclosed herein;

DETAILED DESCRIPTION OF THE INVENTION

Figure 2:
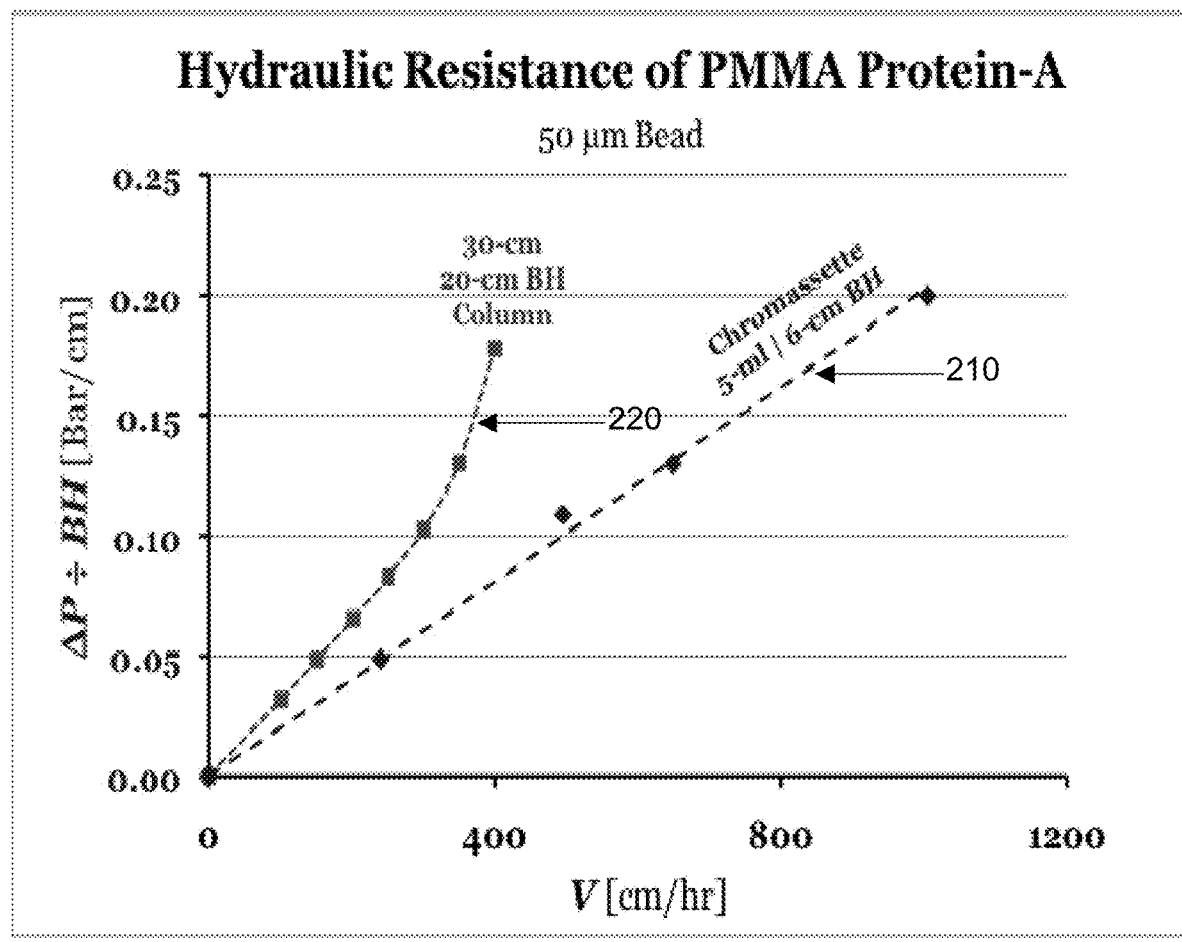
FIG. 2 shows a graph of the hydraulic resistance of 5-ml cassettes compared to that if a conventional chromatography column packed with various beads as a function of the linear velocity.

This invention generally relates to devices and processes suitable for preparative and manufacturing processes, and more specifically to processes used in the manufacture in the pharmaceutical industry for the production of medicinal or therapeutic products. In contrast to conventional devices, the inventor has discovered a way to support adsorptive media in a configuration that is linearly scalable and self supporting and to operate such a device to yield higher productivity compared to conventional systems. Embodiments of the invention utilize planar stackable chromatography cassettes pack with adsorptive media. As used herein, the term soft media generally refers to compressible chromatographic adsorptive media or semi-compressible chromatographic adsorptive media.

Now, referring to FIG. 1A, an exemplary stackable cassette 10 includes an exemplary lattice and distribution network 100 for a stackable chromatography cassette which includes a peripheral seal 101 and is described in more detail in FIG. 1B. The stackable cassette 10 further includes a top plate 110 (also referred to as first plate) and a bottom plate (not shown, also referred to as second plate) on opposite side of top plate. In one embodiment, the second plate is disposed opposite the first plate; the lattice is disposed between the first and second plates and is surrounded on four sides by the peripheral seal. In another embodiment, the peripheral seal 101 and the first plate (top plate 110) and second plate (bottom plate) form a rectangular cuboid.

The lattice and distribution network 100 includes first internal distribution network 102 including first internal distribution channels 116a-116n (collectively a first internal distribution channels 116) and second internal distribution network 106 including second internal distribution channels 118a-118n (collectively a first internal distribution channels 118). The stackable cassette 10 provides access to the distribution channels 116 and 1118 through the top plate 110 to provide distribution of feed stream and collection of eluent stream, respectively. The cassette's 10 lattice and distribution network 100 further includes passageways 104a-104n (collectively passageways 104) with access from the top plate 110 to accept packing retainers (not shown) on the feed end. The cassette's 10 second internal distribution network 106 further includes passageways 108a-108n (collectively passageways 108) with access from top plate 110 to accept packing retainers (not shown) on the eluent end. In this embodiment packing retainers are cylindrical porous rods having a circular cross-section with a diameter approximately equal to the diameter of passageways 104 and 108. Once inserted, the packing retainers are sealed and remain in place. Packing retainers with cross-sections different from a circle are possible. Cassette 10 also includes o-ring well 109 which with an o-ring (not shown) or other sealing mechanism seals the cassette 10 to a holder (FIG. 6) and also seals adjacent cassettes to each other when stacking multiple cassettes.

Now, referring to FIG. 1B, the exemplary lattice and distribution network 100 for a stackable chromatography cassette 10 of FIG. 1A includes the peripheral seal 101, at least one screen 103 forming a lattice 105 surrounded by the peripheral seal 101. The lattice and distribution network 100 further includes the first internal distribution network 102 and a second internal distribution network 106 (FIG. 1A) fluidly coupled to the lattice and surrounded by the peripheral seal 101. The first internal distribution network 102 and the second internal distribution network 106 are connected through the top plate 110 and bottom plate (not shown) to provide distribution of feed stream and collection of eluent stream, respectively. In this embodiment the first internal distribution network 102 and the second internal distribution network 106 also form a pass through distribution network 120 having channels 122a-122n, affecting distribution between cassettes and thereby enabling the stacking of the cassettes.

The cassettes can be packed with various resin types and bead designs and sizes. The cassettes can be operated in several operating modes, including but not limited to:
Batch, multiple cycles/batch;
Continuous operation;
SMB, 8 columns, 3 columns, 2 columns; and
Hyper-Productive operation (described below in more detail).

The support capability of the lattice may be characterized by the specific surface area of the lattice σ (or simply, specific surface area), defined as the wetted surface area of the lattice divided by the void volume of the lattice, $$\sigma = \frac{A_L}{V_L} \quad (1)$$

where $A_L$=wetted surface area of the lattice;
$V_L$=void volume of the lattice;
For a conventional chromatography column:

$$\sigma = \frac{A_L}{V_L} \quad (1')$$

$$\sigma = \frac{4}{D_c}$$

where $D_c$=column diameter.

Embodiments of lattices as disclosed herein, have a specific surface area greater than about 1 cm$^{-1}$, greater than about 3 cm$^{-1}$, greater than 10 cm$^{-1}$, and even greater than 20 cm$^{-1}$ in various embodiments. The larger the specific surface area the greater the support of the chromatographic adsorptive bed provided by the lattice. However, the size of the open cells within the lattice generally are larger than the size of the beads, placing an upper bound on the maximum allowable specific surface are for a given bead size. It is understood that for a given adsorptive chromatographic packed bed, bead sizes are oftentimes not uniform and therefore the term average bead size is sometimes used herein. Generally the characteristic size of the openings in any orientation (the characteristic size of the open cells, hereafter denoted as "d") should be larger than about 5 average bead diameters. For example, a circular opening would have an area greater than: $\frac{1}{4} \pi d^2$; where d=five average bead diameters. In another embodiment d is 10 average bead diameters. It is understood that resin beads are polydisperse, meaning that the population of beads have a range of sizes with considerable variation (the term "bead" and "particle" are used interchangeably and include spherical beads, irregular particles, or even rod-like particles that have a fiber structure).

In one embodiment, on average the distance of any bead to the nearest support element is approximately about 8 to about 20 bead diameters. In another embodiment, a distance between pairs of struts forming each of the open cells is larger than about 5 average diameters of the plurality of adsorptive beads.

The cross-sectional dimensions and shape of the struts affect the specific surface area of the lattice, as well as what fraction of the total volume is void volume vs. structural volume. In some embodiments the struts have a square or rectangular cross-sectional profile with a cross-sectional dimension less than 3 mm; in other embodiments the struts can be less than 1 mm and in still other embodiments less than 0.7 mm. The size and shape of the struts may be limited by the fabrication technology used to fabricate the lattice, but struts can have any cross-sectional configuration.

Since the lattices and cassettes are linearly scalable and stackable, the cassettes provide: low hold-up volume, a stable, robust bed even when packed with soft chromatographic media (e.g., compressible beads), and the ability to operate at high velocity (e.g., greater than 500 to over 1000 cm/hr).

In one exemplary embodiment, the cassette can be operated using a hyper-productive chromatography process which is characterized by very fast cycles, high velocities exceeding and low residence times. In one embodiment the residence time in the loading step is one minute and the process operates at a total cycle productivity of approximately 60 to 90 g/L/hr (GLH) in a bed having a volume greater than 0.5 liter. In yet another embodiment, the hyper-productive process operates at productivities greater than approximately 90 GLH using 30 μm beads and a residence time in the loading step of less than 0.5 minute, and in another embodiment a residence time as low as 0.25 minutes.

The steps for hyper-productive processing in one embodiment include:
providing a stackable chromatographic cassette;
loading a sample to be processed;
operating the chromatographic cassette having an adsorptive bed volume greater than about 0.5 liter by establishing a flow at a linear velocity greater than about 500 cm/hr;
with the residence time of the loading step being less than about one minute.

In certain embodiments the cassette has short beds (less than about 10 cm in length) operated at high velocities (greater than about 1000 cm/hr) and higher pressures (greater than about 3 Bar) in order to obtain the improved productivity. In another embodiment five to six times higher productivity can be obtained with Amsphere™ A3 50 μm beads (Manufactured by JSR Corporation) using the cassettes described herein and operated in hyper-productive mode (i.e., at high velocities and pressures resulting in high productivity).

In various embodiments, the Chromassette cassettes can be packed with any commercially available resin bead (e.g., hydrogel media. polymeric media, semi-compressible adsorptive media, compressible adsorptive media) Cassettes can be packed with multiple resin beads: agarose Protein-A media; cation exchange media; anion exchange media; mixed-mode media; size-exclusion chromatography ("SEC") media; controlled-pore glass ("CPG") media; Amsphere™ A2 and A3 Protein-A beads (JSR Corporation), MabSelect™ Sure Protein-A, SP Sepharose HP cation-exchange and Sepharose Q FF anion-exchange beads (GE Healthcare), YMC 25 & 75 μm cation-exchange beads (YMC Corporation), as well as 30 μm Q Fractogel anion-exchange beads (EMD Millipore Corporation).

FIG. 2 is a graph of hydraulic resistance 210 of 5-ml, 6 cm bead height cassettes compared to the hydraulic resistance 220 of a conventional chromatography column packed with the same bead as a function of the linear velocity. Since the cassette and the column have different bed heights, the hydraulic resistance is shown in a normalized manner as the pressure gradient, pressure drop divided by bed height, for each chromatographic device. As is evident from FIG. 2, the hydraulic resistance of the cassette is constant (a constant slope indicating a linear pressure drop even for velocities exceeding 1000 cm/hr; in contrast, the hydraulic resistance of the conventional column increases with velocities exceeding about 300 cm/hr, becoming quite large even at velocities exceeding 400 cm/hr. For hyper-productive processing, the cassettes are operated at a constant hydraulic resistance independent of velocity.

Figure 3:
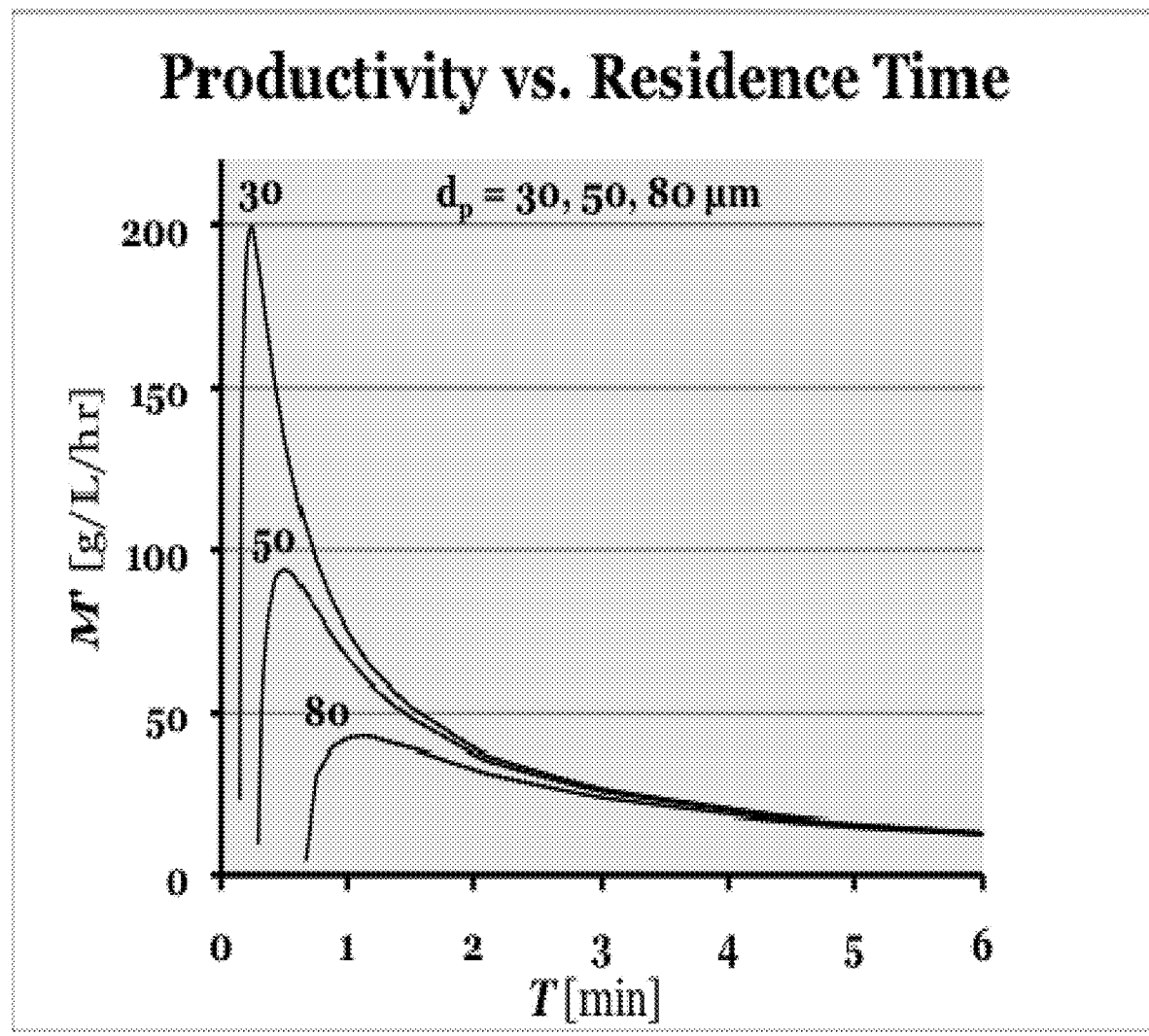
FIG. 3 shows a graph of productivity versus residence time for several bead diameters according to embodiments disclosed herein according to mathematical modeling.

FIG. 3 shows a graph of productivity versus residence time for several bead diameters according to certain mathematical models of capture and release processes. In a hyper-productive process using a cassette, productivity is a dependent variable, and productivity depends on velocity, residence time, bed volume media type. For smaller beads (30 micron) high productivity (about 200 g/L/hr) can be obtained with residence times as short as 0.25 seconds.

Figure 4:
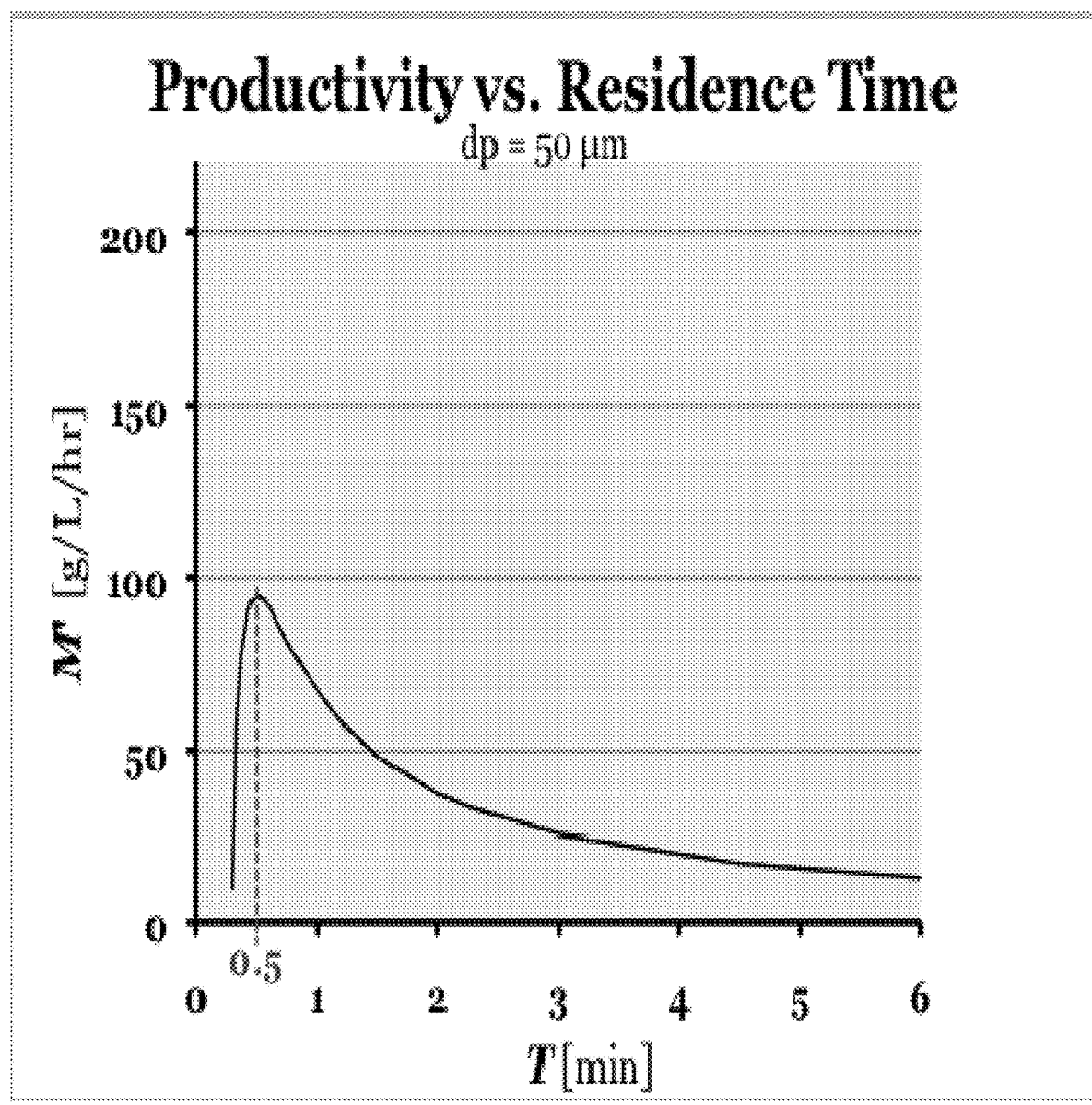
FIG. 4 shows a graph of productivity versus residence time for a 50 micron bead diameter according to embodiments disclosed herein according to mathematical modeling.
Figure 5:
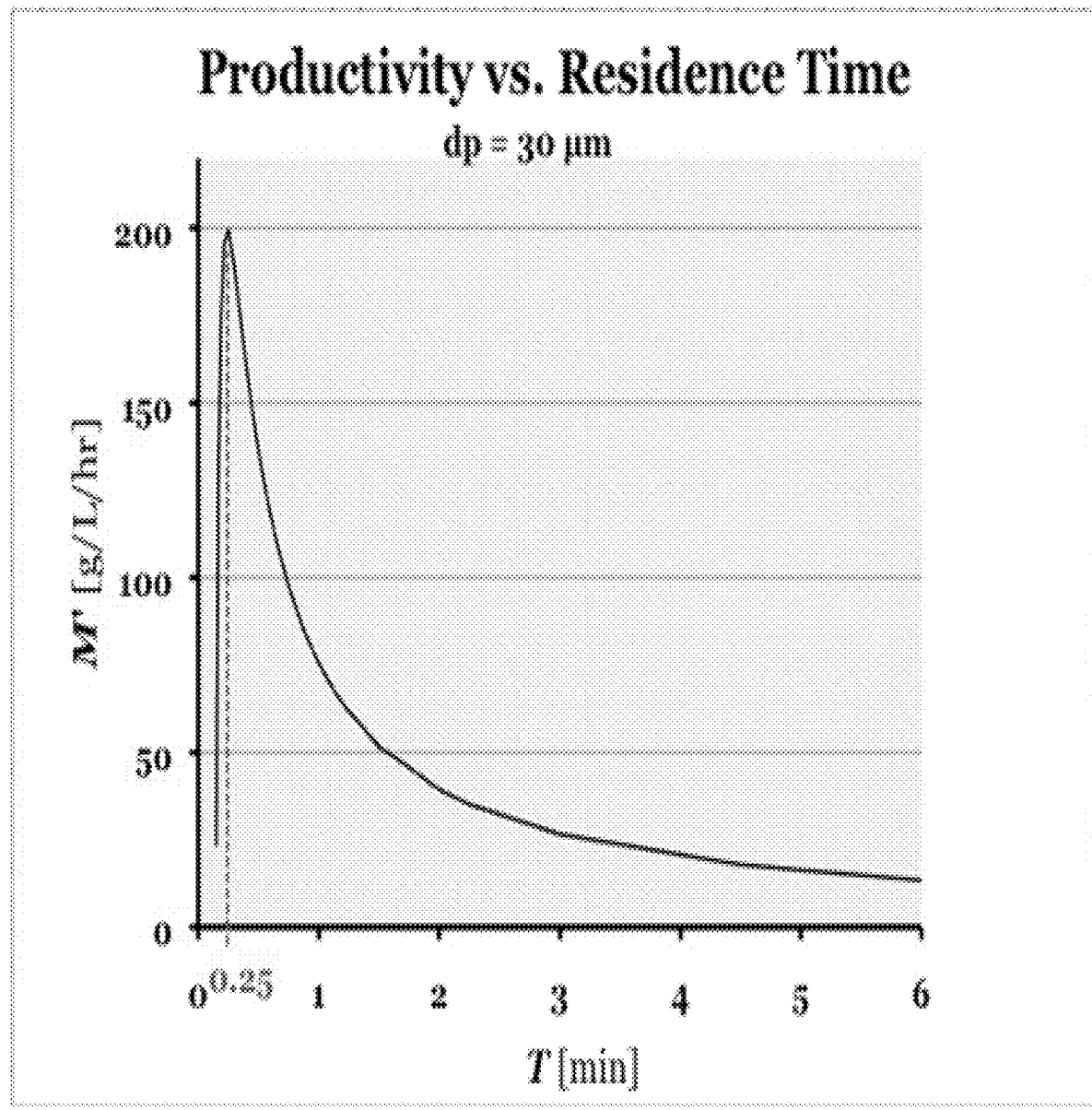
FIG. 5 shows a graph of productivity versus residence time for a 30 micron bead diameter according to embodiments disclosed herein according to mathematical modeling.

FIG. 4 shows a graph of productivity versus residence time for a 50 micron bead diameter. FIG. 5 shows a graph of productivity versus residence time for 30 micron bead diameters. For these smaller beads (30 micron) high productivity (about 200 g/L/hr) can be obtained with residence times as short as 0.25 seconds. The data in FIGS. 2-5 reflects the support feature of the cassette lattice 105. Variations of the hyper-productive process are also possible. In one technique the fluid streams in the process steps may be run in opposite directions. For example, the feed stream in the load step may be run in the "forward" direction of the cassette, whereas the elution stream may be run in the "reverse" direction. While conventional chromatography columns are not capable of being run in the reverse direction without a high risk of voiding, adsorptive devices of this invention can be run in the reverse direction without voiding.

Figure 6:
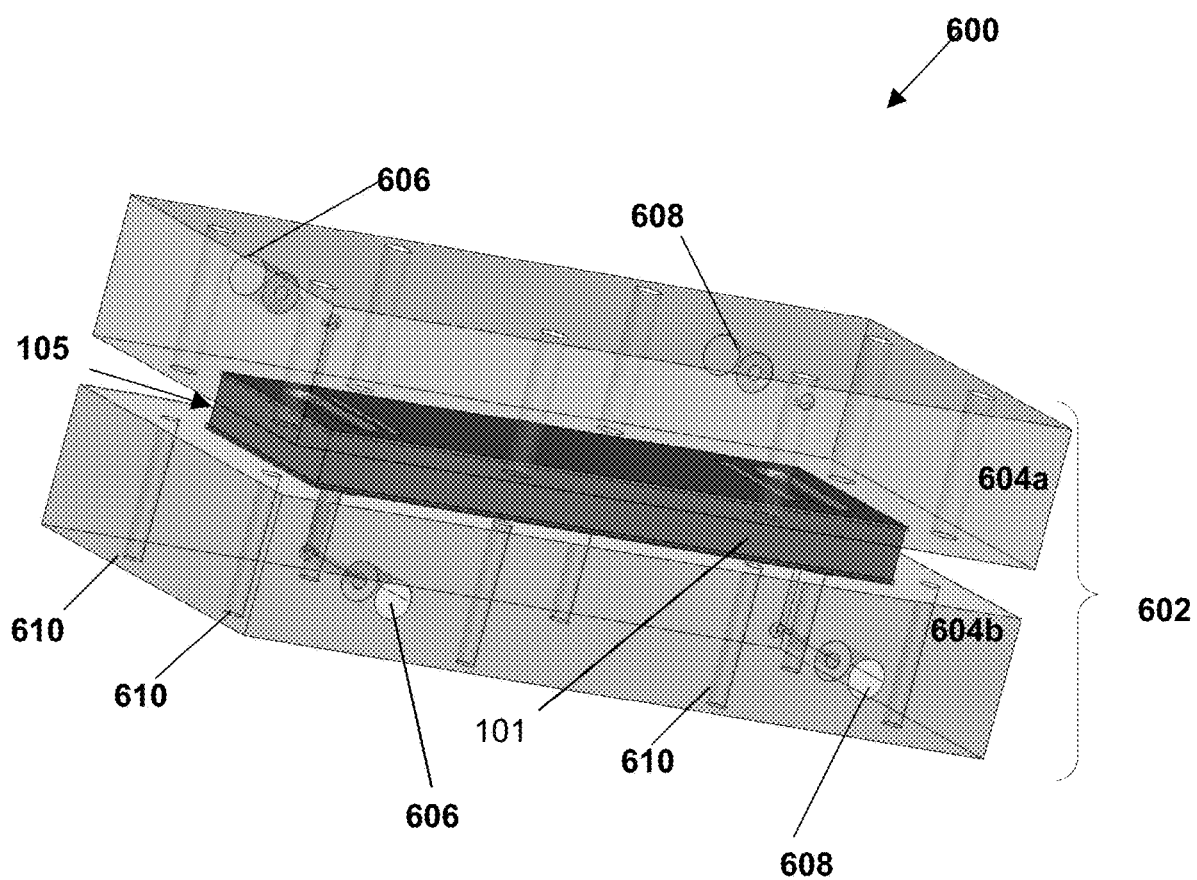
FIG. 6 is a view of a system including cassette holder and a cassette according to embodiments disclosed herein.

Now referring to FIG. 6, in one embodiment a system 600 for hyper-productive chromatography includes a chromatography cassette 105 mounted in a scalable chromatographic cassette holder 602 (also referred to as holder 602). Chromassette cassette 10 is mounted within the holder 602 to support the planar surfaces and to feed/collect the feed and eluent streams. It is understood that multiple (i.e., stacked) cassettes can be mounted in parallel within the holder 602. The holder 602 includes upper 604a and lower 604b segments (collectively referred to as segments 604). The segments 604 include feed passageway 606 and an eluent passageway 608. The holder 602 segments 604 and secured using fasteners (not shown) which are inserted through assembly slots 610.

In other embodiments, manifolds are integrated into the holder 602 and are reusable. Here the holder 602 segments 604 may be machined from a clear plastic (e.g., polycarbonate) or a non-clear polymer (e.g., nylon) or from a metal (e.g., 316 stainless steel (SS) or 3D-printed materials. In various embodiments a chromatographic cassette includes a housing which acts as a holder or shell (having a peripheral seal and top/bottom plates.

The cassettes can be configured in parallel, series or series parallel. In other embodiments the cassettes are inoculated with a fine micro-particulate dispersion designed to selectively plug the frits in order to fine-tune the hydraulic resistance of a cassette. Using some of the techniques described above large scale cassettes (e.g., one liter, five liters or 100 liters) can be produced either as a single unit or a combination of smaller cassettes Stackable chromatographic cassettes disclosed herein can be fabricated by different processes. In one process, the stackable chromatographic cassette includes a lattice and a chamber which are fabricated with 3-D printers. In one embodiment, Fused Deposition Modeling (FDM) printing technology is used, but other printing technologies can also be used. Since FDM printing uses an extrusion process, areas between adjacent extruded layers make FDM printed objects inherently porous. It is difficult to make an impervious surface with FDM printing. The chamber surrounding the lattice needs to be impervious (i.e. leak free) under fluid pressure, therefore, additional processing is used to seal the porous chamber in certain embodiments. One process to seal the chamber is encapsulation in a suitable sealant (e.g., epoxy or urethane). Other secondary processes (e.g., machining, including CNC machining) are used to fabricate features with a higher resolution than possible with FDM printing. The combination of FDM printing, sealing, and machining (referred to as a Hybrid FDM printing process) can produce an impervious cassette with features that allow stackability and the desired chromatographic performance.

Figure 7A:
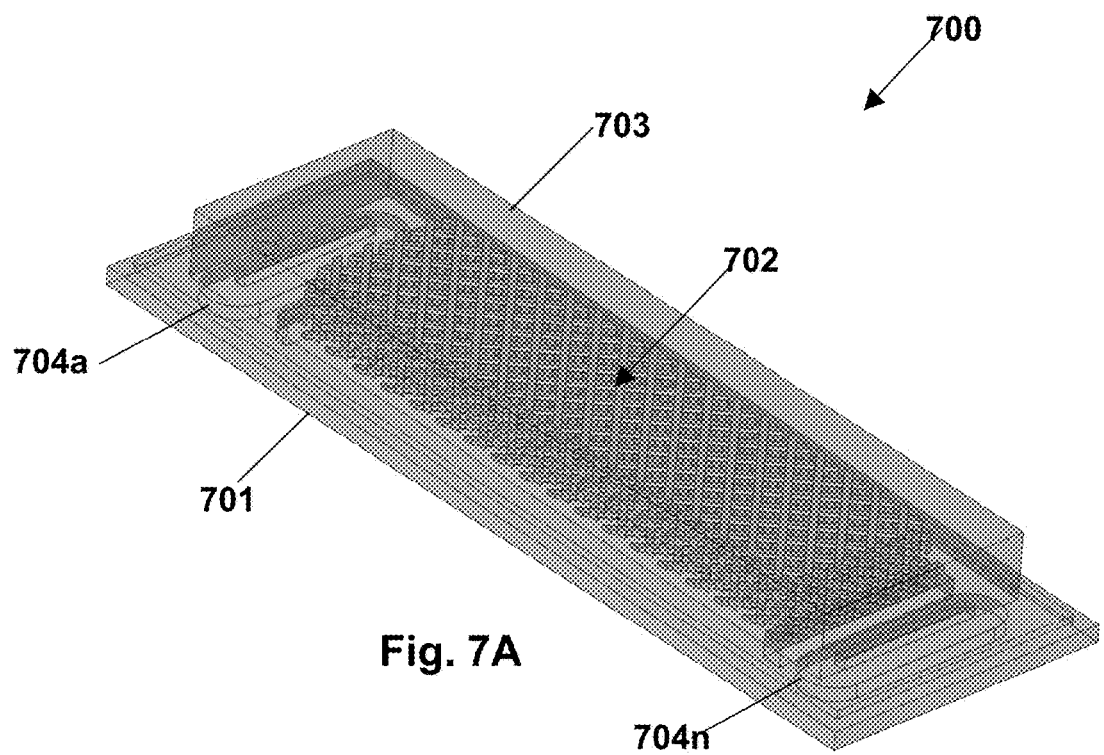
FIG. 7A is a view of a portion of a stackable chromatography cassette including a print plate, lattice and chamber enclosure according to embodiments disclosed herein.

Referring to FIG. 7A, a portion of an exemplary stackable chromatographic cassette 700 includes a printing plate 701 disposed on the printing plate 701, a lattice 702 and a chamber enclosure 703 surrounding the lattice 702. In some embodiments printing plate 701 is machined or molded and used as a printing platform for FDM printing the lattice 702 and the chamber enclosure 703. In other embodiments plate 701 is FDM printed along with the lattice 702 and the chamber enclosure 703. Plate 701 may have features 704a-704n (collectively features 704) formed on/in the plate 701 by machining, molding or FDM printing. These features 704 include, but are not limited to, o-ring wells, packing retainer slots, and distribution passageways.

Figure 7B:
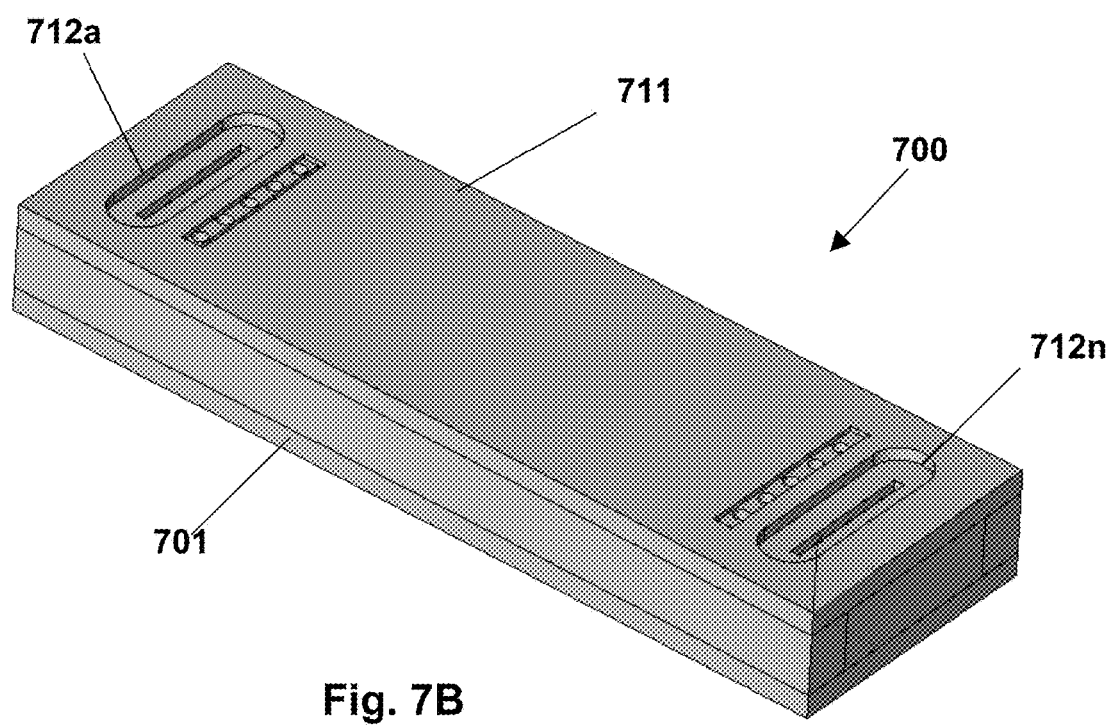
FIG. 7B is a view of the stackable chromatography cassette of FIG. 7A which has been completed with a covering shell according to embodiments disclosed herein.

Now referring to FIG. 7B, the complete stackable chromatographic cassette 700 includes plate 701, chamber enclosure 703 (not shown), lattice 702 (not shown) and a shell 711 covering the chamber enclosure 703 and the lattice 702. The shell 711 includes features 712a-712n formed in and on shell (collectively features 712) and similar to features 704. Shell 711 may be formed by a casting process using epoxy, by insert molding or by other molding processes known in the art. Features 712 are formed either by the mold in which shell 711 is formed or by secondary machining. Shell 711 seals chamber enclosure 703 in one embodiment by encapsulating the exterior of chamber enclosure 703.

In other embodiments the chamber enclosure 703 is sealed by impregnating the interior of chamber enclosure 703 with a suitable sealant. In these embodiments the chamber enclosure 703 is filled with the sealant in a manner that displaces the air and induces complete wetting of the interior of the chamber enclosure 703, followed by withdrawal of all the excess sealant leaving behind sealant that fills small cavities in the chamber interior and chamber enclosure. The impregnation process is carried out under conditions that selectively leave sealant in the areas which contribute to porosity while displacing excess sealant from the void spaces in the lattice and the distribution networks. Process conditions to ensure such selectivity are (a) a low sealant viscosity and (b) a low velocity during sealant withdrawal. Some embodiments use sealants with viscosities of less than 200 centipoise (cP), in other embodiments less than 100 cP and in still other embodiments less than 30 cP. In some embodiments sealant withdrawal velocities less than 100 cm/min are used, in some embodiments sealant withdrawal velocities less than 30 cm/min are used, and in still other embodiments sealant withdrawal velocities less than 10 cm/min are used. In some embodiments sealants may be diluted in a suitable solvent to reduce the viscosity of the sealant; in these embodiments the sealant is removed by evaporation before the sealant fully cures.

In other embodiments, the sealant includes, but is not limited to epoxy, polyurethane, silicone or UV-curable adhesive and the sealant is applied to one or both of an outside surface of the chamber enclosing the lattice and an inside surface of the chamber enclosing the lattice, where the sealant impregnates wetted surfaces of the chamber and excess sealant is withdrawn before the excess sealant cures.

In another embodiment, the lattice is fabricated using a 3D-printer followed by encapsulation with a lower-melting thermoplastic to form the shell: peripheral seal and top and plates. Once the lattice is fabricated it is encapsulated/over molded with a lower-melting or similar thermoplastic to form the shell: peripheral seal and top and plates. Frit and distributor holes are drilled into the overmolded shell, followed by insertion and sealing of the frits. FDM 3-D printing technology also enables 3D-printing the packing retainer or fits and printing the distributor holes, further simplifying the process. The fabrication of another embodiment includes drilling of frit and distributor holes into an overmolded shell, followed by sealing of the frits. Such a process produces an overmolded lattice, uses lower cost materials and can be printed by a relatively low-cost printer. Other embodiments include combinations of molded plates to form the lattice combined with 3D printed holders, 3D printed frits.

It is understood that although the embodiments described herein relate specifically to bio-molecular applications, the principles, practice and designs described herein are also useful in other applications, including the manufacture of vaccines and biopharmaceuticals. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A method of performing a Hyper-Productive chromatography process comprising:
    providing a stackable chromatographic cassette;
    loading a sample to be processed;
    operating the stackable chromatographic cassette having an adsorptive chromatographic bed having a volume greater than 0.5 liter by establishing a flow at a linear velocity greater than 500 cm/hr;
    and
    wherein a residence time of the loading step is less than one minute.

2. The method of claim 1 wherein the adsorptive chromatographic bed comprises one of:
    a polymeric media;
    a hydrogel media;
    a compressible adsorptive media; and
    a semi-compressible adsorptive media.

3. The method of claim 2 wherein the polymeric media is polymethylmethacrylate (PMMA).

4. The method of claim 1 wherein the linear velocity is greater than 1000 cm/hr.

5. The method of claim 1 wherein the residence time in the loading step is less than 0.5 minute.

6. The method of claim 1 wherein the residence time in the loading step is less than 0.25 minute.

7. A method of performing a Hyper-Productive chromatography process comprising:
    providing at least one chromatographic cassette having an adsorptive chromatographic bed having a bed volume greater than one liter and comprising one of:
    compressible chromatographic adsorptive media;
    semi-compressible chromatographic adsorptive media;
    soft chromatographic adsorptive media;
    placing the at least one chromatographic cassette in a cassette holder;
    loading a sample to be processed;
    operating the chromatographic adsorptive bed establishing a flow at a velocity greater than 1000 cm/hr; and
    wherein a residence time in the loading step is less than one minute.

8. The method of claim 7 wherein the residence time in the loading step is less than 0.5 minutes.

9. The method of claim 7 wherein the residence time in the loading step is less than 0.25 minutes.

10. The method of claim 7 wherein soft chromatographic media comprises one of:
   polymethylmethacrylate (PMMA);
   agarose Protein-A media;
   cation exchange media;
   anion exchange media;
   mixed-mode media;
   size-exclusion chromatography ("SEC") media;
   controlled-pore glass ("CPG") media.

11. The method of claim 7 further comprising operating the chromatographic cassette having a linear pressure drop over a velocity range of zero cm/hr to about 1200 cm/hr.

12. The method of claim 7, further comprising operating at a total cycle productivity of greater than about 60 g/L/hr (GLH), with media having a average bead size less than about 50 μm at velocities greater than about 500 cm/hr.

13. The method of claim 7, further comprising operating at a total cycle productivity of greater than 100 g/L/hr (GLH) with media having a average bead size less than about 40 μm at velocities greater than about 800 cm/hr.

14. The method of claim 7, further comprising operating at a total cycle productivity of greater than 150 g/L/hr (GLH) with media having a average bead size less than about 30 μm at velocities greater than about 1000 cm/hr.

15. The method of claim 7, wherein the adsorptive chromatographic bed comprises chromatographic beads having an average bead size less than 30 μm.

16. The method of claim 7 further comprising stacking a plurality of chromatographic cassettes within the cassette holder to form a chromatographic adsorptive bed having a scaled up bed volume larger than about five liters.

17. The method of claim 7 further comprising operating at a constant hydraulic resistance independent of velocity.

18. A system for performing a Hyper-Productive chromatography process comprising:
   a scalable chromatographic cassette holder;
   wherein the stackable chromatographic cassette is disposed in the scalable chromatographic cassette holder;
   wherein the stackable chromatographic cassette is capable of being operated according to claim 1.

19. The system of claim 18, wherein the stackable chromatographic cassette comprises an fused deposition modeling (FDM) 3-D printed lattice having porous printed surfaces sealed with a sealant.

20. The system of claim 19, wherein the sealant is one of:
   epoxy;
   polyurethane;
   silicone; and
   UV-curable adhesive.

21. The system of claim 19 further comprising a chamber enclosing the lattice; and
   wherein the sealant is applied to one of:
      an outside surface of the chamber enclosing the lattice; and
      an inside surface of the chamber enclosing the lattice, where the sealant impregnates wetted surfaces of the chamber and excess sealant is withdrawn before the excess sealant cures.

* * * * *